United States Patent [19]

Nakata et al.

[11] Patent Number: 4,982,158
[45] Date of Patent: Jan. 1, 1991

[54] METHOD AND APPARATUS FOR MAGNETIC DETECTION OF FLAWS

[75] Inventors: Roy Nakata, Palo Alto; Mario Rabinowitz, Redwood City, both of Calif.; Lawrence D. Nottingham, Charlotte, N.C.

[73] Assignee: Electric Power Research Institute, Inc., Palo Alto, Calif.

[21] Appl. No.: 211,337

[22] Filed: Jun. 23, 1988

[51] Int. Cl.⁵ .................. G01N 27/83; G01R 33/12
[52] U.S. Cl. ............................. 324/263; 505/1; 324/248
[58] Field of Search .............. 324/248, 263, 232–243; 505/845, 846, 843, 700, 702, 704, 705, 706, 1

[56] References Cited

U.S. PATENT DOCUMENTS

| | | | |
|---|---|---|---|
| 4,087,749 | 5/1978 | McCormack | 324/263 X |
| 4,613,816 | 9/1986 | Zeamer | 324/248 |
| 4,683,419 | 7/1987 | Neuelmann et al. | 324/263 X |
| 4,700,135 | 10/1987 | Hoenig | 324/248 |
| 4,703,265 | 10/1987 | Törnblom | 324/232 |
| 4,725,778 | 2/1988 | Brown | 324/263 |
| 4,823,082 | 4/1989 | Nasu et al. | 324/232 |

FOREIGN PATENT DOCUMENTS

| | | | |
|---|---|---|---|
| 2827203 | 1/1980 | Fed. Rep. of Germany | 324/263 |
| 0746278 | 7/1980 | U.S.S.R. | 324/263 |

OTHER PUBLICATIONS

Rabinowitz, "Quantum–Gas Model Estimate for Wide Range of Superconducting Critical Temperatures", Int'l. Jrnl. of Theo. Physics (Plenum Press), vol. 28, No. 2, pp. 137–146, Feb. 1989.

Rabinowitz, "Superconductivity and Electric Power", Forum for Applied Research and Public Policy, Spring 1988, pp. 55–62.

Primary Examiner—Reinhard J. Eisenzopf
Assistant Examiner—Warren S. Edmonds
Attorney, Agent, or Firm—James B. Hinson

[57] ABSTRACT

An array of SQUID detectors to map the magnetic field associated with test currents flowing in the component to be tested. The SQUID is an ultrasensitive, miniature device that transduces a faint magnetic field to a measurable voltage. Perturbation occurs in the test currents and the associated magnetic field at physical defects or inhomogeneities. Multi-dimensional test currents are injected into the component being tested; the injection being made between specific electrodes by varying the direction of the current until it is normal to the direction of the defect to maximize and amplify the effect of the perturbation. The perturbation is detected by the SQUID grid which pinpoints the location, orientation, and size of the defect. The frequency of the injected current can be made to sweep the spectrum from DC to the highest response limit of the SQUID to scan for defects at various depths. As the frequency increases, "skin effect" decreases the depth of the test current permitting multi-dimensional profiles of the defect to be imaged. Computer processing permits high resolution images of inhomogeneities to be produced.

47 Claims, 5 Drawing Sheets

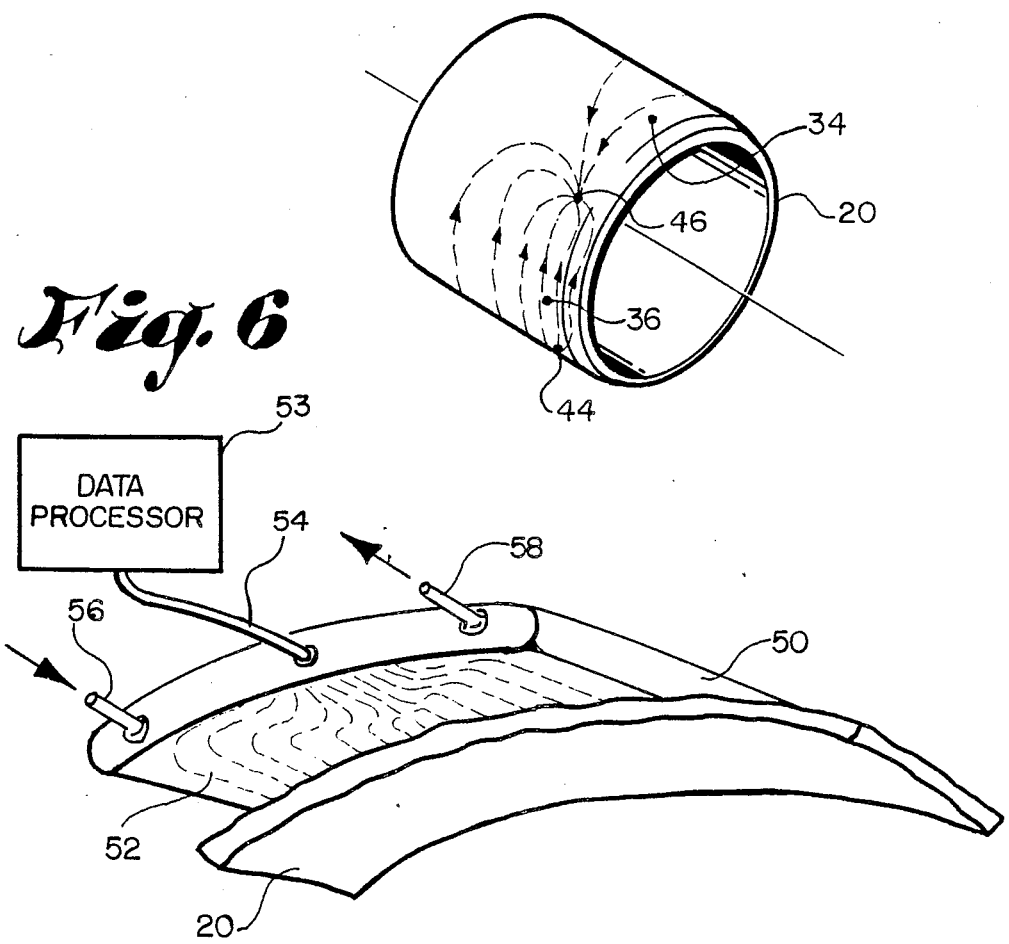
Fig. 6
Fig. 7
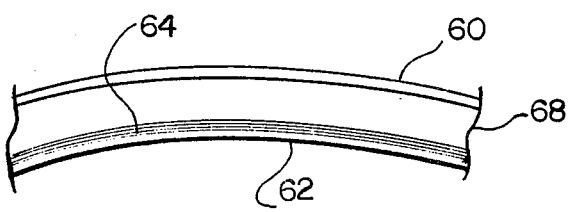
Fig. 8

METHOD AND APPARATUS FOR MAGNETIC DETECTION OF FLAWS

FIELD OF THE INVENTION

The invention relates to detectors, and more specifically to the use of Superconducting Quantum Interference (SQUID) arrays, for mapping the magnetic field associated with multi-dimensional test currents, and means to analyze the magnetic map to locate inhomogeneities in electrically conductive or electrically semiconductive materials.

DEFINITIONS

"Detectable inhomogeneities" in the content of this patent refers to any structural feature of the component being tested which may be located by mapping the magnetic field associated with multi-dimensional test currents.

The word "flaw" encompasses all types of unintentional imperfections embodied in the component to be tested. Examples of "flaws" include cracks, unintended structural variations and other imperfections.

For purposes of the preferred embodiment of the invention, "multi-dimensional test current" is defined as any electric current intentionally introduced into the component to be tested which has characteristics which may be selectively varied sequentially, such as frequency, amplitude, orientation or direction. In alternative embodiments of the invention the term includes any electric current which establishes a magnetic field within or surrounding the component to be tested which may be detected by a suitably positioned array of detectors to produce signals which may be analyzed to either locate or determine the characteristics of a detectable inhomogeneity.

DESCRIPTION OF THE PRIOR ART

Inhomogeneities intentionally produced as part of the manufactured item or resulting from flaws in electrically conductive or semiconductive components present difficult inspection problems. Additionally, in some components made of these materials inhomogeneities such as cracks may not be detectable when the component is removed from the assembly in which it is used. This is particularly true in situations where an inhomogeneity such as a crack may not be detectable except under stress. Removing the component from the assembly can result in removal of the stress, rendering the crack undetectable using conventional test means.

Typical prior art testing techniques for detecting these inhomogeneities utilized a limited number of test current paths defined by current injection points and low sensitivity sensors. The result was that in many cases the test current paths were not oriented at a favorable angle with respect to the abnormality. Such a technique could result in flaws not being detected in that the process was not sensitive to defects substantially parallel to the test current path. Additionally, conventionally used testing techniques failed to provide reliable information related to the depth of the defect. These and other undesirable characteristics of prior art testing systems are substantially alleviated by the present invention as described in more detail below.

SUMMARY OF THE INVENTION

In practicing the preferred embodiment of the invention, a magnetic field is established in the space adjacent to at least one surface of the component to be tested by one or more multi-dimensional test currents flowing in the component. Multi-dimensional test currents are selected to enhance the sensitivity of the system by favorably orienting at least one of the multi-dimensional test currents to the probable flaws. The practicality of the multi-dimensional test currents is enhanced in the case of rotating electrical machinery such as generators and motors by the fact that testing for flaws may be done in-situ. Each multi-dimensional test current distributes throughout the component being tested, and produces a magnetic field having predetermined relationship to the multi-dimensional test current in the space adjacent to at least one surface of the component being tested. The specific distribution of each of the multi-dimensional test currents is determined by the technique used to produce the current, the design of the component being tested and the uniformity of the electrical conductivity characteristics of the material utilized in manufacturing the component.

A SQUID sensor, array positioned adjacent to the surface of the component, detects the magnitude of the magnetic field produced by each of the test currents, and produces a data array having a predetermined relationship to the detected magnetic fields. Structural inhomogeneities in the material used to construct the component being tested result in one or more of the test currents exhibiting abnormal flow patterns with corresponding abnormal variations in the magnetic fields, as detected by the sensor array.

Alternating (AC) test currents may also be used to produce the multi-dimensional test current. In such cases the test current can be concentrated near the surface of the component being tested as a result of the well known "skin effect". Varying the frequency of the current from zero cycles to high frequency permits information related to the depth of the crack to be determined, as the skin depth is inversely proportional to the square root of frequency. Furthermore, test currents having different characteristics, in addition to continuous wave frequency, such as single or repetitive pulses may also be applied sequentially, with the magnetic fields associated with each of these currents separated by suitably processing the data base. One may expect additional sensitivity for pulsed currents as the current path is altered in real time detection as it approaches the flaw. In any case, it is possible to process the data related to the depth of a fault to produce a three dimension representation of the fault.

An important factor determining the sensitivity of the system is the distance between the defect and the SQUID detectors and the magnitude of the multidimensional test current. As the distance between the SQUID detectors and the inhomogeneity increase, the decrease in sensitivity may be compensated for by increasing the test current.

Any technique for establishing the test currents is suitable, so long as a data base and corresponding magnetic field map can be established or predicted using the output signals of the SQUID array with the map including sufficient details to permit the integrity of the component to be determined. A specific component may be tested by comparing magnetic maps of the component before and after flaws have occurred, or maps associated with components known to be good to a similar map of the component being tested. The contours of the magnetic map may be predicted using the structural features of the component with deviations indicating faults.

For purposes of reproducibility, test current injection contacts may be plated, plasma sprayed etc. on the component to be tested in a predetermined pattern. Current probes, mechanically held against the current injection contacts, may be used to inject the test currents.

Each multi-dimensional test current flowing in the component to be tested causes a current to flow in all parts of the component. The characteristics (direction and magnitude) of the current flow at any arbitrary point within the component being tested will be determined by the electrical impedance characteristics of the component, the technique used to produce the current and the magnitude of the multi-dimensional test current. (It is necessary to consider the impedance of the component rather than its resistance if AC test currents are used.) A maximum variation in a test current pattern and the resulting magnetic field results when the test current is oriented at an approximately 90 degree angle with respect to orientation of the flaw surface.

Another embodiment would be to connect a plurality of the current injection contacts for sequential current injection with all detectors active in order to image the flaw by means of a technique analogous to X-ray tomography without necessarily comparing the image to a base image.

In the preferred embodiment provisions are provided for injecting the multi-dimensional test current at a variety of locations such that there is a significant probability that the test current will be oriented with respect to flaws resulting in near maximum disturbances in the expected magnetic field at the site of the defect. This feature greatly enhances the sensitivity of the system. Utilizing a variety of differently oriented current injection locations permits randomly oriented faults to be mapped with high sensitivity.

Additionally, it is quite practical that the system or machine using the component itself might be designed such that small tracer currents are naturally introduced into the component to be tested either by operating the device in a test mode or as a part of the normal operation of the device. Such tracer currents may be used as the multi-dimensional test currents, previously described.

Low voltage and low test currents which are made practical by the sensitivity of the SQUID detectors are particularly advantageous in that the voltages are sufficiently low not to cause sparks across defects or to cause carbonization and change in the defect being analyzed.

The diameter of each element of the SQUID array can be very small, for example, in the order of the diameter of a human hair. The individual detectors may be vapor deposited forming a large integrated network of SQUID detectors in the form of a flexible blanket. Positioning the blanket over the surface of the component to be tested permits the individual sensors of the array to be used to measure the magnitude of the magnetic field associated with the test current at predetermined locations in the component being tested. A computerized data processing system connected to the SQUID array collects sufficient data to produce a high resolution map of the magnetic field associated with the test current. Abnormalities in the component correspond to abnormalities in the high resolution map of the magnetic fields. This feature improves the resolution of the system by several orders of magnitude as compared to prior art magnetic testing techniques. The extent of the area of the component mapped is limited by the size of the SQUID array and the data processing capability of the system.

Further improvements in the resolution of the SQUID array is provided by an alternate embodiment which utilizes a plurality of superimposed SQUID arrays. Well known data processing techniques are utilized to accurately determine the magnetic field corresponding to overlapping areas of the elements of the SQUID array. The net effect of this approach is to reduce the effective size of the elements of the SQUID array to the overlapping area of the individual SQUID detectors.

The resolution of the system using overlapping SQUID arrays is a function of the complexity of the SQUID array and the associated data processing. Currently it is believed that multiple layer SQUID arrays having up to two or more layers are practical.

The primary problem being addressed which resulted in the conception of the invention disclosed in this patent application was the detection of cracks in large rotating machines associated with electric power generation. Typical of the components which may be tested are retaining rings, such as those subsequently discussed. Therefore, the invention is described with respect to such a use. However, it will be appreciated by those skilled in the art that the invention has many other uses. The invention can be adapted to test other components made of conducting or semiconducting materials. A partial list of components which could be tested include nuclear fuel rods and graphite control rods for nuclear power plants; airplane structures such as wings; other structures subject to stress and vibration such as bridges and buildings. The miniaturization of the SQUID detector permits insertion inside structures such as wings and nuclear pipes as well as on their exterior. The term "component" used in this application includes all these specific structures and other devices made of electrically conducting and/or electrically semiconducting materials.

Basic SQUID technology is rapidly developing. Significant among recent developments has been an increase in the operating temperature of the SQUID sensors. Practical SQUID sensors are currently available which are operable up to about 77K.

In many applications of the invention, so called high temperature SQUIDS offer significant advantages in that they require less cooling. For example, when arrays of SQUID detectors are mounted in close proximity to an object at a higher temperature, heat transfer between the object and the SQUID array significantly increases the task of cooling the array. For the same heat transfer the spacing for a 77K SQUID is approximately 1/20 as large as the spacing for a 4K SQUID. Closer proximity to the test specimen permits increased sensitivity and resolution for flaw detection. High temperature SQUIDS may be made of $Y_1\ Ba_2\ Cu_3O_{7-y}$ (transition temperature, $T_c > 94K$), $Bi_2\ Sr_{3-x}\ Ca_xCu_2\ O_{8+y}$ ($T_c > 110K$), $Tl_2\ Ba_2\ Ca\ Cu_2\ O_8$ ($T_c > 120K$), or other high $T_c$ materials.

It is also well known that as the operating temperature of the SQUID detector increases, the noise (sometimes referred to as Johnson noise) increases. The seriousness of this noise increases as the frequency increases. In most applications envisioned by the current invention, this noise increase is not a serious problem because the SQUID detectors will be operated in the lower frequency ranges. Additionally, the use of arrays permit data processing to be used to improve the effective sensitivity, as compared to the sensitivity of an individual SQUID detector of a given coil size.

DESCRIPTION OF THE DRAWINGS

FIG. 6 is a retaining ring illustrating the injection of a test current using a pair of current injection contacts selected from a plurality of possible contacts.

FIG. 7 is a pictorial diagram illustrating a blanket of SQUID arrays connected to a data processor.

FIG. 8 is a cross-section of a portion of the blanket illustrated in FIG. 7.

DETAILED DESCRIPTION

Figure 1:
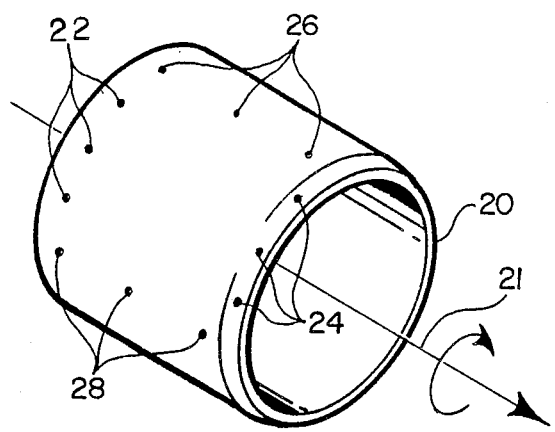
FIG. 1 is a retaining ring of an electric power generator illustrating the placement of typical current injection contacts.

A typical retaining ring 20 for an electric power generator is illustrated in pictorial diagram, FIG. 1. Typically, retaining rings have a diameter in the order of 4 feet and a length of 3 feet. Testing of a retaining ring 20 is a typical application of the invention. Therefore, the invention is described with respect to such an application.

In use, retaining rings are positioned on the rotor of the generator using shrink fit techniques. As is general knowledge in the art, these assembly techniques result in hoopstress of the retaining ring 20, caused by the stretched state of the ring as well as the radial force transmitted from the body onto which the ring is mounted. In the static state the stress increases from the exterior surface of the retaining ring 20 toward the interior. Moreover this stress distribution changes as the rotor (onto which the retaining ring is mounted) rotates at high operational speed.

Generally, cracks which result from the stresses begin on the interior of the retaining ring 20 and extend outward as a result of the stress patterns described above. Additionally, removal of the retaining ring 20 from the rotor thus relieving the stress, may cause cracks on the interior to close and not be detectable using any conventional means. Therefore in-situ diagnostics as made possible by this invention, are greatly preferable and needed. A typical retaining ring 20 may be tested in accordance with the invention described herein with sufficient sensitivity to detect cracks not visible from or extending to the exterior surface and not detectable using prior art testing techniques. Whereas the retaining rings, by prior art test methods, may have to be removed from the rotor for inspection, the method of this invention will permit inspection with the retaining ring in-situ.

To facilitate testing, in accordance with the techniques disclosed therein, the retaining ring 20 has a plurality of test current injection contacts formed on the exterior surface thereof. As an example of the method, three typical points 22 are located in a row along a first edge of the retaining ring 20. Similarly three additional test current injection contacts 24 are located in a second row along the second edge of the retaining ring 20. Two rows, each including three test current injection contacts which will inject current transversely to the axis of rotation 21 of the retaining ring 20 as respectively illustrated at reference numerals 26 and 28. Selected areas of the surface of the retaining ring 20 may be plated using a metal to form the test current injection contacts.

In utilizing the invention, at least one test current is injected between a plurality (at least a pair) of the current injection contacts. More specifically, in FIG. 2 a first current injection probe 30 and a second current injection probe 32 are positioned in electrical contact with first and second current injection contacts 34 and 36. The current injection probes, 32 and 36, are provided with a suitable test current from a current source, not illustrated for reasons of simplicity, causing a test current to flow in the retaining ring 20 in a pattern typically illustrated by dotted lines in FIG. 2. The density and direction of the dotted lines in FIG. 2 respectively correspond to the magnitude and direction of the test current. That is to say that the portions of the retaining ring 20 having a larger test current density flowing therein are indicated by dotted lines which are closer spaced than those portions of the retaining ring having a lower test current density.

It should also be noted that even though the single (composite) test current is injected at only two points in this example, the composite test current divides and distributes over the retaining ring 20 such that test currents flows in essentially all portions of the retaining ring 20 with the magnitude and direction of the test current in each path having a predetermined relationship to the electrical impedance along that path. Factors determining the electrical impedance along any arbitrary path between an arbitrary pair of current injection contacts include the length of the path, the material of which the retaining ring is constructed, the dimensions of the retaining ring 20, the integrity of the retaining ring 20 along the test current path and deliberate electrical insulation placed between adjacent parts, such as between the retaining ring and the copper windings of the rotor. In particular this method is advantageous for in-situ diagnosis of retaining rings because there is an insulating layer between the ring and the copper winding system.

Figure 2:
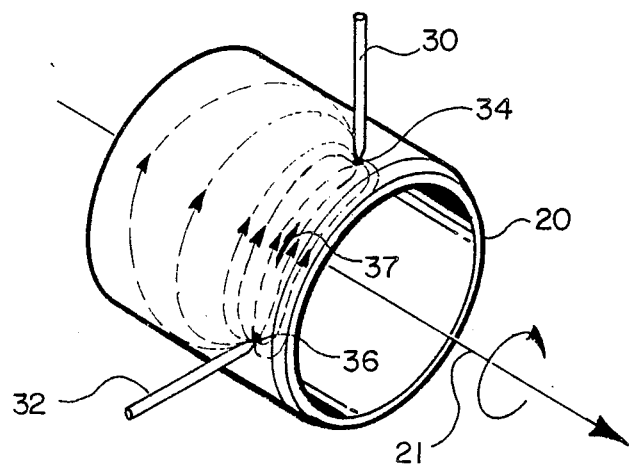
FIG. 2 is a drawing of the retaining ring, illustrated in FIG. 1, including an illustration of the current distribution (which produces a magnetic field) resulting from injection of a test current utilizing at least a pair of typical current injection contacts.

Inhomogeneities such as a typical crack 37 which may be essentially parallel to the test current flow have little effect on the impedance of the path. However cracks which are essentially perpendicular to the natural current flow path of the test current significantly increase the impedance along the path and reduce the test current density flowing in the component in an area near the crack 38 (illustrated in FIGS. 3 and 4). The magnetic field associated with each test current path and each point thereof is measured along the exterior surface of the retaining ring 20 to produce a map of the magnetic field having a predetermined relationship to the associated test currents and inhomogeneities in the retaining ring 20. The magnetic field at a plurality of points along the surface of the retaining ring is detected by a SQUID 50 (FIG. 7) array to produce a data base which is analyzed to determine the structural integrity of the retaining ring 20 as more specifically described below. However, the specific test current patterns illustrated in FIG. 2 are not particularly effective in detecting the crack 37. This example illustrates one of the limitations of typical prior art systems.

Figure 3:
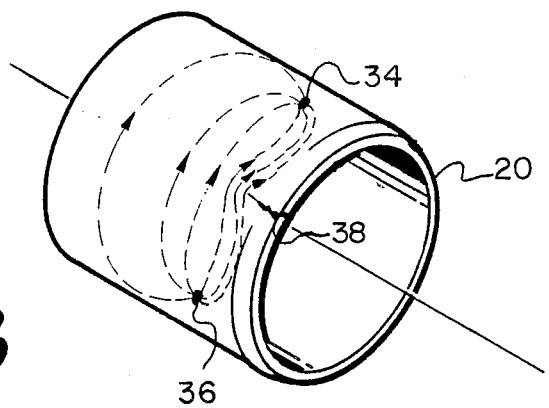
FIG. 3 is a retaining ring indicating the modification in the test current flow pattern as a result of a typical crack in the retaining ring.
Figure 4:
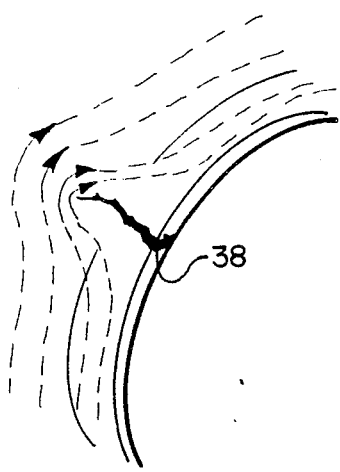
FIGS. 4 and 5 are drawings illustrating the change in the test current flow pattern as the width of the crack increases.
Figure 5:
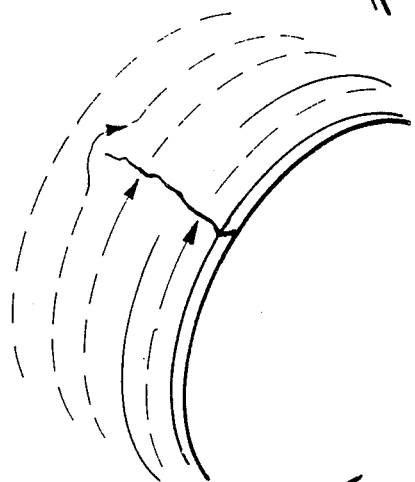

FIGS. 3, 4, and 5, indicate disturbances to be expected in the test current flow patterns and the magnetic fields resulting therefrom as a result of a typical crack 38, which is substantially parallel to the axis of rotation 21 the retaining ring 20 and perpendicular to the test currents. In this figure, the test current injection probes 30 and 32 are not illustrated for purposes of simplifying the drawings.

More specifically, the crack or defect 38 extending from the edge of the retaining ring 20 towards its interior and across the path of the test current resulting in an increase in the electrical impedance of the retaining ring 20. This causes the test current to deviate around the crack 38 and increase in density near the tip of the crack 38. In extreme circumstances, the test current density zero along the outer edge of the retaining ring 20. Specifically, the extreme situation is illustrated in FIG. 4 where the crack 38 has progressed to a point where no electrical contact is made between opposing surfaces of the crack 38. This results in the current along the edge decreasing to zero. Conversely, as illustrated in FIG. 5, some electrical contact may be maintained between the edges of the crack with the current decreasing along the edge and increasing along the tip of the crack 38.

FIG. 6 illustrates that multiple test current may be injected using different pairs of current injection contacts. More specifically, in this illustration, a first test current is injected using a second pair of current injection contacts, 44 and 46. The first test current previously illustrated and discussed may simultaneously be injected using test current injection contacts 34 and 36. Since this test current was previously discussed with reference to FIG. 2, it is not illustrated in this drawing, for reasons of simplicity.

Suitable SQUID arrays can be formed in an overlay such as blankets which conform to a portion or all of the outer surface of the retaining ring 20. A typical blanket is illustrated in FIG. 7 at Reference Numeral 50 with respect to a portion of the retaining ring 20. The SQUID detectors are arranged in rectangular patterns corresponding to dotted lines 52 and coupled to a data processing or collection systems such as a data processor 53 (digital computer system) using a cable 54. As is conventional in the art, the array must be cooled by flowing a suitable coolant in the cooling input port 56 and out the cooling output port 58. A cross-section of a typical section of the blanket is shown in FIG. 8. The blanket includes an outer and inner protector cover 60 and 62, which must be sufficient to retain the coolants and provide suitable mechanical protection for the SQUID detectors.

This array approach improves the reliability of the test method since it may be important not only to detect a fault, but also the location of the fault. If a single element SQUID is used, a change in signal at different times might be due to mislocation in set up rather than the formation of a fault. Whereas the SQUID array will not permit such errors because by having many reference points (all of which could be spanned simultaneously by the elements of the array) the output from the unaffected reference points would easily assure that the SQUID array was precisely repositioned back to its previous test location.

The SQUID array is formed on the inner surface of the protective coating 62 as illustrated at Reference Number 64. Space between the SQUID array 64 and the upper cover 60 is provided for the coolant to flow as indicated at Reference Numeral 68. Interface wiring between the computer port 54 and the SQUID array 64 can be provided using any convenient technique so long as it doesn't interfere with the cooling of the SQUID array.

Figure 9:
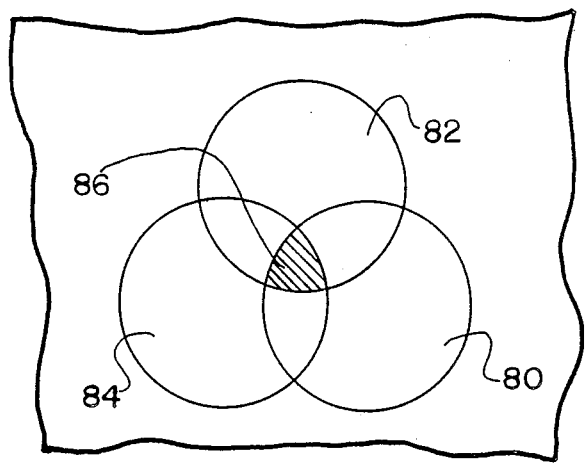
FIG. 9 is a cross-section drawing of a multilayer SQUID array including overlapping SQUID detectors.

Alternatively, the SQUID array may comprise a plurality of overlying arrays of detectors with the detectors comprising each layer offset with respect to the detectors of the other arrays. More specifically, such an arrangement is illustrated in FIG. 9 with respect to three typical SQUID detectors, 80, 82, and 84. Each of the arrays are positioned such that any three SQUID detectors with each detector selected from a different array are sensitive to the magnetic field present in a common overlapping area 86, which is less than the active area of any of the three SQUID detectors, 80, 82, and 84. Output signals from the SQUID detectors are processed by a digital computer to improve the resolution of the magnetic map to correspond to this area.

Direct cooling of each SQUID element or array of SQUID elements is also possible by use of microminiature refrigeration systems built into or attached to the integrated network of SQUIDS rather than the double-walled blanket.

Although this technique of improving the resolution of the system has been illustrated with respect to three layers, it will be appreciated by those skilled in the art that more layers may be used to further improve the resolution.

Figure 10:
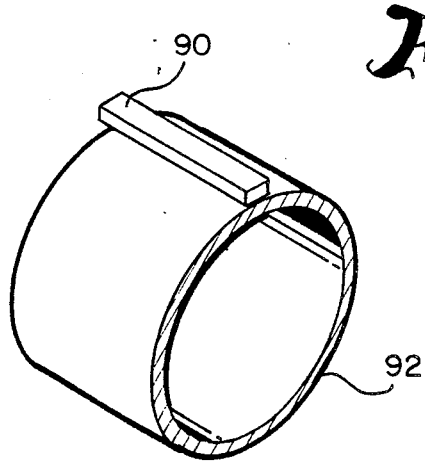
FIG. 10 is a drawing illustrating the use of a linear array of SQUID detectors.
Figure 11:
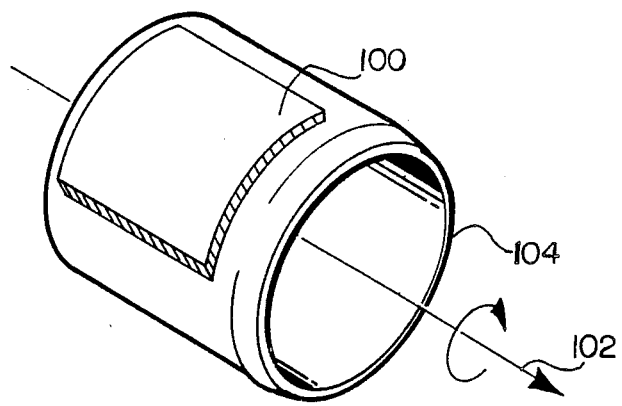
FIG. 11 is a drawing illustrating a first embodiment of the invention which uses an induction coil to induce the multi-dimensional test currents.
Figure 12:
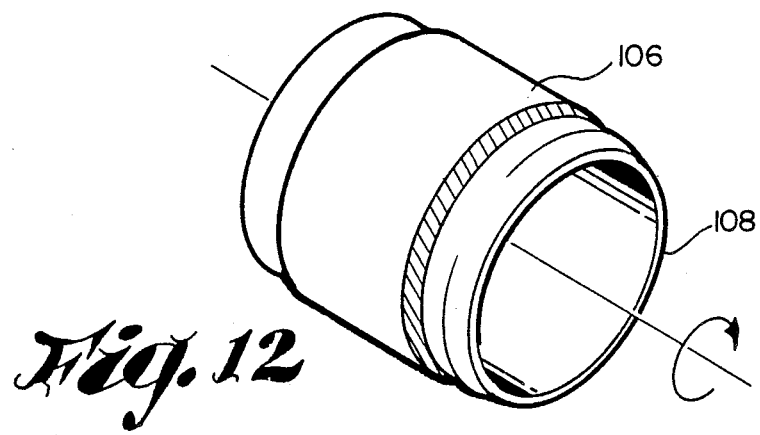
FIG. 12 is a drawing which illustrates a second embodiment of the invention which uses an induction coil to induce the multi-dimensional test currents.
Figure 13:
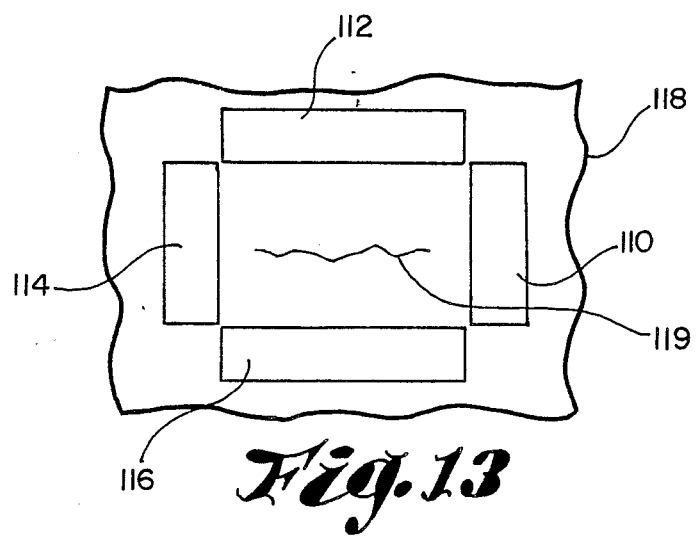
FIG. 13 is a drawing which illustrates an alternate arrangement of the multi-dimensional test current injection contacts.
Figure 14:
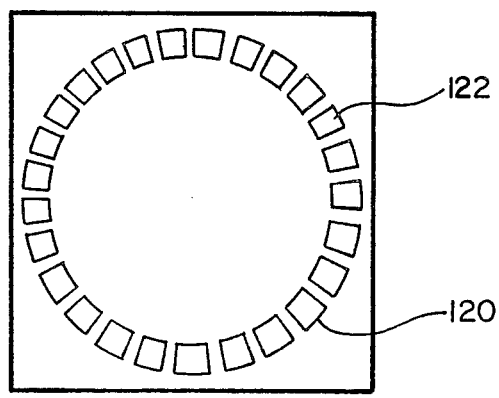
FIG. 14 is a drawing which illustrates another alternate embodiment of the multi-dimensional test current injection contacts.

Various alternate features and embodiments of the invention are illustrated in FIGS. 10 through FIG. 14. More specifically, FIG. 10 illustrates an alternate arrangement of the SQUID array, FIGS. 11 and 12 illustrate alternate means of producing the multi-dimensional test currents and FIG. 13 and FIG. 14 illustrate alternate arrangements of the current injection contacts.

In FIG. 10 an elongated array 90 of SQUID detectors is held in a fixed position as the retaining ring 92 is rotated. Multi-dimensional test currents are produced in the retaining ring 92 by any suitable means. As the retaining ring 92 rotates data is collected to produce a map of the magnetic field over its surface.

Test currents may also be injected into the component to be tested using techniques not requiring any direct electrical connection to the component. Typical examples of such techniques include the use of current carrying induction coils positioned in a predetermined relationship to the component to be tested. Two examples of usable induction coils are illustrated in FIGS. 11 and 12.

In FIG. 11, the axis of the induction coil 100 is substantially perpendicular to the axis of rotation 102 of the retaining ring 104. By contrast, in FIG. 12 the axis of the induction coil 106 is substantially parallel to the axis of rotation of the retaining ring 108.

Alternatively, it should be emphasized that the current injection pads previously discussed may be randomly shaped and located at randomly selected locations so long as the selected locations result in suitable test currents flowing in all portions of the component to be examined. For example, in FIG. 13 four elongated current injection contacts 110, 112, 114 and 116 are affixed in a rectangular configuration to a portion 119 of a typical retaining ring. A first contact pair 110 and 114 is oriented perpendicularly to the axis of rotation of the retaining ring. Similarly a second contact pair 112 and 116 is oriented substantially parallel to the axis of rotation. As previously explained, probable orientation of a typical stress crack 119 in the retaining ring 118 is substantially parallel to the axis of rotation. A multi-dimensional test current injected using contact pair 110 and 114 will experience a minimum disturbance. Similarly, a multi-dimensional test current injected using contact pair 112 and 116 will experience a maximum disturbance. Overall sensitivity of the system is enhanced by processing data axis of differently oriented multi-dimensional test currents together with maximum sensitivity resulting when the test currents are oriented with respect to the flaw so as to achieve a correlation between maximum and minimum perturbations.

One simple technique is to produce a composite magnetic map which is the part-by-part difference of two maps. Other processing techniques are also possible. Other arrangements or elongated current injection pads are also usable. Any pair or any three of these current injection pads may be used to inject the multi-dimensional test current.

Another configuration of usable current injection contacts is illustrated in FIG. 14. In this configuration, the current injection test contacts are arranged along a closed curved path, which may be a circle with two typical contacts illustrated at reference numerals 120 and 122.

The above test current injection patterns are examples only.

We claim:

1. A system for detecting structural inhomogeneities in a component to be tested, comprising in combination:
   (a) means for selectively establishing at least one multi-dimensional test current in said component to produce a magnetic field detectable adjacent to the surface of said component;
   (b) means for selectively and sequentially changing at least one parameter of said multi-dimensional test current, said at least one parameter being selected from a list which includes,
      (1) the frequency of said multi-dimensional test current;
      (2) the amplitude of said multi-dimensional test current;
      (3) the orientation of said multi-dimensional test current with respect to said component;
   (c) means for detecting the magnitude of said magnetic field at a plurality of locations adjacent to said surface of said component to form a selected number of data arrays having a predetermined relationship to the electrical conductivity characteristics of said component; and
   (d) means for analyzing said data arrays to determine if said component includes structural inhomogeneities.

2. A system for detecting structural inhomogeneities in a component in accordance with claim 1 wherein said means for establishing said at least one multi-dimensional test current includes a plurality of test current injection contacts which may be selected and used in pairs to selectively inject multi-dimensional test currents into said component with each multi-dimensional test current injected utilizing different pairs of said test current injection contacts and flowing along selected and different paths.

3. A system in accordance with claim 2 wherein the major current paths associated with at least first and second pairs of said test current injection contacts intersect at a selected angle.

4. A system in accordance with claim 3 wherein said selected angle is in the order of 90 degrees.

5. A system in accordance with claim 1 wherein selected ones of said multi-dimensional test currents have different characteristics permitting the magnetic fields associated therewith to be distinguished from each other.

6. A system in accordance with claim 5 wherein said different characteristics are selected to permit information related to the depth of said inhomogeneity to be obtained.

7. A system in accordance with claim 1 wherein said means for detecting said magnetic field includes a predetermined number of individual SQUID detectors.

8. A system in accordance with claim 7 wherein said predetermined number of SQUID detectors comprises a plurality of SQUID detectors arranged in an array of a predetermined pattern.

9. A system in accordance with claim 8 wherein said array of SQUID detectors are arranged and mounted in the form of a flexible blanket which may be shaped to substantially conform to a first surface of said component.

10. A system in accordance with claim 9 wherein said means for analyzing each of said plurality of data arrays includes means for forming a map of the intensity contour of the magnetic field resulting from said test currents along said at least one surface of said component.

11. A system in accordance with claim 10 wherein said means for analyzing each of said plurality of data bases includes means for analyzing said maps to identify portions having abnormal characteristics.

12. A system in accordance with claim 11 further including micro-refrigeration means for cooling members of said SQUID array.

13. A system in accordance with claim 11 wherein means for analyzing each of said plurality of data bases includes means for analyzing said maps to identify abnormal flow patterns in said multi-dimensional test currents.

14. A system in accordance with claim 13 wherein inhomogeneities in said component are located by identifying changes in the flow pattern of said multi-dimensional test currents which are the result of said inhomogeneities.

15. A system for detecting inhomogeneities in a component, comprising in combination:
   (a) means utilizing at least one multi-dimensional test current to establish a magnetic field having a selected magnitude and a selected orientation in said component;

(b) means for selectively changing said selected orientation;

(c) means for detecting the magnetic field in a plane having a predetermined relationship to a surface of said component to produce a data array; and (d) means for analyzing each of said data arrays to determine the location and characteristics of said inhomogeneity.

16. A system for detecting inhomogeneities in a component comprising in combination;

(a) means for injecting at least one multi-dimensional test current into said component, said multi-dimensional test current having parameters including frequency, amplitude and orientation with respect to said component which may be selectively and sequentially varied;

(b) means for selectively and sequentially varying said parameters;

(c) means for detecting the magnetic field associated with said multi-dimensional test current comprising two or more arrays of SQUID detectors with members of said arrays off-set such that the responsive area of selected members of said arrays partially overlap to produce at least first and second data bases; and (d) means for analyzing said data bases to produce a magnetic map having a resolution higher than similar maps produced using a reduced number of data bases.

17. A system for producing a multi-dimensional image of inhomogeneities in a component, comprising in combination:

(a) means for establishing a sequential plurality of multi-dimensional test currents in the component to be tested, each of said plurality of multi-dimensional test currents having parameters which may be selectively changed;

(b) means for selectively varying said parameters;

(c) means for producing a multi-dimensional map of the magnetic fields associated with said multi-dimensional test currents; and (d) means for analyzing said multi-dimensional maps to produce a multi-dimensional image of said inhomogeneities.

18. A system for detecting inhomogeneities in a rotating component, comprising in combination:

(a) means for establishing a predetermined pattern of multi-dimensional test currents in said rotating component, said multi-dimensional test currents having parameters including frequency, orientation and amplitude which can be selectively and sequentially varied;

(b) means positioned at a fixed location relative to said rotating component to detect magnetic fields related to said multi-dimensional test currents to form a data array;

(c) means for analyzing said data array to detect any inhomogeneities in said rotating component.

19. A system in accordance with claim 18 wherein said means to detect magnetic fields includes an array of micro-refrigeration cooled SQUID detectors.

20. A system in accordance with claim 19 wherein said SQUID detectors are designed to operate at a temperature above 20K.

21. A system for detecting structural inhomogeneities in a component in accordance with claim 20 wherein said multi-dimensional test currents are injected utilizing a plurality of current injection contacts which are selected in at least pairs with selected ones of said multi-dimensional test currents flowing along different paths.

22. A system in accordance with claim 21 wherein the major test current paths associated with at least first and second pairs of said multi-dimensional test current injection contacts are selected to intersect at a selected angle.

23. A system in accordance with claim 22 wherein said selected angle is selected to be in the order of 90 degrees.

24. A system in accordance with claim 23 wherein the characteristics of selected ones of said multi-dimensional test currents are selected to permit the magnetic fields associated therewith to be distinguished from each other.

25. A system in accordance with claim 24 wherein said different characteristics are selected to permit information related to the depth of said inhomogeneities to be obtained.

26. A method for detecting inhomogeneities in a component, comprising the steps of:

(a) producing at least one multi-dimensional test current having selectively variable parameters in said component to establish a magnetic field having a selected magnitude and a selected orientation in said component;

(b) detecting said magnetic field in a plane having a predetermined relationship to a surface of said component to produce a data array; and (c) analyzing each of said data array to determine the location, depth and characteristics of said inhomogeneities.

27. A method for detecting structural inhomogeneities in a component to be tested, comprising the steps of:

(a) selectively establishing at least one multi-dimensional test current having selectively variable parameters in said component to produce a magnetic field detectable adjacent to the surface of said component;

(b) detecting the magnitude of said magnetic field at a plurality of locations adjacent to a surface of said component to form a selected number of data arrays having a predetermined relationship to the electrical conductivity characteristics of said component; and (c) analyzing said data arrays to determine if said component includes structural inhomogeneities.

28. A method in accordance with claim 27 further including the step of positioning a plurality of SQUID detectors at predetermined locations adjacent said surface of said component to detect said magnetic field.

29. A method in accordance with claim 28 further including the step of arranging said SQUID detectors in an array having a predetermined pattern.

30. A method in accordance with claim 29 further including the step of mounting said SQUID detectors on a flexible blanket which may be shaped to substantially conform to a first surface of said component.

31. A method in accordance with claim 30 further including the step of further analyzing said data array to produce a map of the intensity contour of the magnetic field resulting from said multi-dimensional test currents along said at least one surface of said component.

32. A method in accordance with claim 31 further including the step of selectively analyzing said maps and identifying portions corresponding to said inhomogeneities.

33. A method in accordance with claim 32 further including the step of analyzing said magnetic maps to identify locations corresponding to abnormal multi-dimensional test currents flow patterns.

34. A method in accordance with claim 33 further including the step of identifying changes in the flow pattern of said multi-dimensional test currents which are the result of said inhomogeneities.

35. A method in accordance with claim 32 further including the step of utilizing micro-refrigeration means for cooling members of said SQUID array.

36. A method for detecting inhomogeneities in a component, comprising in combination:
   (a) producing at least one multi-dimensional test current having selectively variable parameters in said component;
   (b) detecting the magnetic field produced by said multi-dimensional test current utilizing two or more arrays of SQUID detectors with members of said arrays off-set such that the action response of selected members of said arrays partially overlap to produce first and second data basis; and
   (c) analyzing said data bases to produce a magnetic map having a resolution higher than similar maps produced using a reduced number of data bases.

37. A method for producing a multi-dimensional image of inhomogeneities in a component, comprising in combination:
   (a) producing at least one multi-dimensional test current having selectively and sequentially variable parameters in the component to be tested; (b) detecting the magnetic fields associated with said at least one multi-dimensional test current to produce a multi-dimensional map of the magnetic fields; and
   (c) analyzing said multi-dimensional maps to produce a multi-dimensional image of said inhomogeneities.

38. A method for detecting inhomogeneities in a rotating component, comprising the steps of:
   (a) establishing a predetermined pattern of at least one multi-dimensional test current having selectively and sequentially variable parameters in said rotating component;
   (b) detecting the magnetic fields produced by said one or more multi-dimensional test currents at a selected fixed location to produce a data array; and
   (c) analyzing said data array to detect any inhomogeneities in said rotating component.

39. A method in accordance with claim 38 wherein said means to detect magnetic fields includes an array of micro-refrigeration cooled SQUID detectors.

40. A method in accordance with claim 38 including the further steps of:
   (a) processing said at least first and second data bases to produce first and second magnetic maps;
   (b) processing said first and second magnetic maps to identify regions of maximum and minimum magnetic field intensity; and
   (c) correlating said signals of maximum and minimum magnetic field intensity to identify flaws in said component being tested.

41. A method in accordance with claim 38 wherein said component is a retaining ring.

42. A method in accordance with claim 41 wherein said surface is an interior surface of said retaining ring.

43. A method in accordance with claim 42 wherein said multi-dimensional test current is pulsed.

44. A method in accordance with claim 38 wherein said rotating electrical machine is an electric current generator.

45. A method in accordance with claim 38 wherein said rotating machine is an electric motor.

46. A method in accordance with claim 38 wherein said surface is an interior surface.

47. A method of testing at least one component forming a part of rotating electrical machines, comprising the steps of:
   (a) establishing at least a plurality of multi-dimensional test current in said component, a first one of said multi-dimensional test currents having a first orientation with respect to the axis of rotation of said retaining ring, a second one of said multi-dimensional test currents having a second orientation with respect to the axis of rotation of said retaining ring, said first orientation differing from said second orientation;
   (b) utilizing a plurality of sensors positioned adjacent a surface of said component to produce at least first and second data bases, said first and second data base respectively having first and second predetermined relationships to the flow pattern of said first and second positions of said multi-dimensional test currents;
   (c) processing said first and second data bases to produce data having a predetermined relationship to the integrity of said retaining ring.

* * * * *